United States Patent [19]
Graham et al.

[11] Patent Number: 5,994,492
[45] Date of Patent: Nov. 30, 1999

[54] MICROGELS

[75] Inventors: Neil Bonnette Graham, Bearsden, United Kingdom; Jianwen Mao, Grenzach-Wyhlen, Germany

[73] Assignee: University of Strathclyde, Glasgow, United Kingdom

[21] Appl. No.: 08/930,652

[22] PCT Filed: Apr. 4, 1996

[86] PCT No.: PCT/GB96/00863

§ 371 Date: Dec. 11, 1997

§ 102(e) Date: Dec. 11, 1997

[87] PCT Pub. No.: WO96/31551

PCT Pub. Date: Oct. 10, 1996

[30] Foreign Application Priority Data

Apr. 4, 1995 [GB] United Kingdom .................. 9506946

[51] Int. Cl.⁶ ..................................... C08G 18/48
[52] U.S. Cl. .............................. 528/76; 424/486; 526/75; 523/353
[58] Field of Search ............................... 528/76; 424/486; 526/75; 523/353

[56] References Cited

U.S. PATENT DOCUMENTS

| 3,850,880 | 11/1974 | Hakanson et al. | 528/76 |
| 4,293,679 | 10/1981 | Cogliano | 528/48 |

FOREIGN PATENT DOCUMENTS

| 0 121 331 | 10/1984 | European Pat. Off. . |
| 0 132 384 | 1/1985 | European Pat. Off. . |
| 2090264 | 10/1984 | United Kingdom . |
| 80/01985 | 10/1980 | WIPO . |
| 91/02763 | 3/1991 | WIPO . |

*Primary Examiner*—Rachel Gorr
*Attorney, Agent, or Firm*—Alston & Bird LLP

[57] ABSTRACT

A microgel is produced by a two-stage process wherein the monomers are first polymerized in the absence of solvent for a controlled period, and in a second stage solvent is added and polymerization is completed. The polymer is preferably a polyurethane formed from a polyalkylene glycol, a triol and a diisocyanate. The molecular weight is typically 100,000 to 200,000. The microgels form granules which may be compressed into solid form. Such solid forms containing an active agent, such as a protein, are useful as sustained delivery devices.

33 Claims, 4 Drawing Sheets

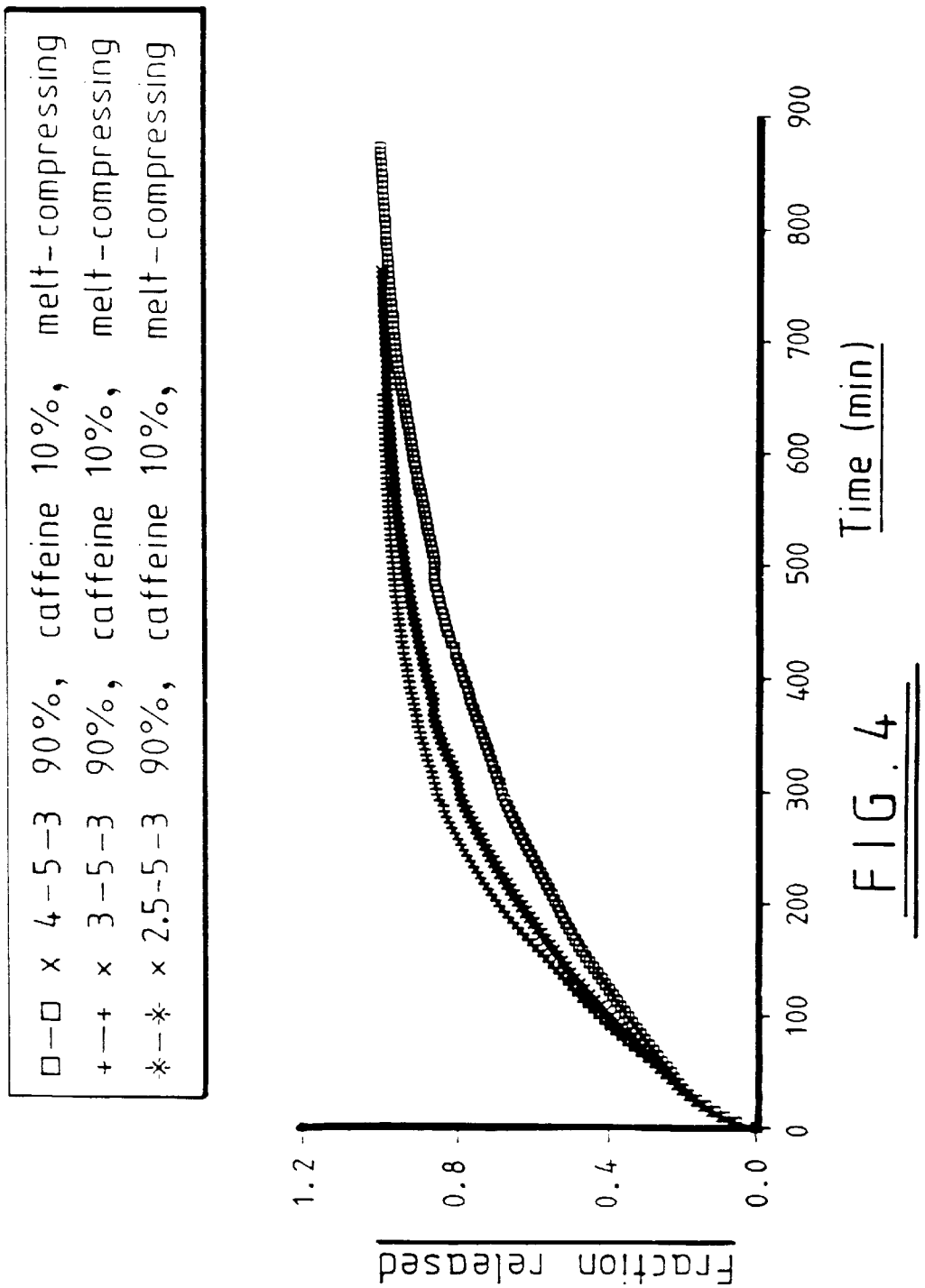

MICROGELS

FIELD OF THE INVENTION

The present invention relates to a process for the production of a microgel. The process enables the production of microgels in a simple and economic manner. The invention also relates to microgels themselves, particularly when compressed or melted into a solid body.

BACKGROUND

Prior patent specification GB2090264 discloses a solution polymerisation process for the preparation of polymeric materials comprising cross-linked particles which are capable of forming sols, that is to say, a class of hydrogels which are referred to as microgels. The process involves polymerising one or more monomers in a solvent having particular characteristics and terminating the polymerisation before macrogelation occurs.

Microgels may be defined as intramolecularly cross-linked macromolecules. In common with other cross-linked polymers, microgels have a cross-linked structure and fixed surfaces. On the other hand, microgels may generally speaking be dissolved in certain solvents in the same way as non-cross-linked linear or branched polymers of similar molecular weight. In conventional cross-linked polymers, macrogelation occurs such that an extensive three-dimensional network is set up, which generally speaking resists dissolution in solvents. In microgels, the cross-linking structure exists predominantly within individual globular molecules.

The special molecular structure of microgels and their ability to exist as globular particles makes the microgel a promising material for pharmaceutical applications, such as carriers for controlled drug delivery. Patent specifications GB2090264, GB2143733 and GB2230952 disclose sustained release devices comprising an active ingredient and a hydrogel.

It is therefore foreseen that microgels may have a variety of potential industrial uses, and it would be desirable to provide an improved production process capable of producing microgels in a simple efficient and economical manner. Originally, microgels had to be produced at high dilutions which favour intramolecular rather than intermolecular cross-linking. Patent specification GB2090264 exemplifies an improved process for the production of microgels at higher concentrations in solvents having particular defined characteristics and under certain conditions which favour microgel formation. Generally speaking, the microgels formed have good solubility in the solvents used in the production process, so that solid microgel granules are generally obtained by precipitation of the microgel from solution by the addition of an organic liquid such as hexane, cyclohexane, petrol ether or methanol. However, the addition of a further organic liquid to the solvent used in the microgel production reaction means that the solvent cannot be directly reused without costly procedures for recovering the solvent from the mixture formed with the organic liquid. Furthermore, the microgel granule size or shape may not be suitable for direct use as a tabletting excipient, so that further processing such as grinding and sieving may be needed. These expedients are undesirable and detract from the industrial applicability of such microgel production processes.

It is an object of the present invention to mitigate these disadvantages.

SUMMARY OF THE INVENTION

One aspect of the present invention provides a process for the production of a microgel, which comprises (i) in a first step conducting a polymferisation reaction by cross-linking at least one monomer in a reaction mixture substantially free of solvent therefor; and (ii) thereafter in a second step, dissolving the reaction mixture in a solvent and completing the polymerisation to produce a microgel.

Polymerisation may generally be taken to completion without macrogelation occurring, and there is therefore usually no need to terminate polymerisation prior to completion (though this is not excluded).

Another aspect of the present invention relates to the microgel polymer, particularly in granular form. The process of the present invention has been found to provide microgels having higher molecular weights than those obtained by conducting the polymerisation in a solvent in the absence of the solvent-free first polymerisation step.

A third aspect of the invention relates to a sustained release device comprising the microgel and having incorporated therein an active agent to be released. Advantageously, the device is in the form of a compress of microgel granules having the active agent dispersed therethrough. On swelling in water the compress generally becomes microporous but retains its integral structure.

Thus, it is surprisingly found according to the present invention that the use of a solvent-free first stage of the polymerisation enables microgels to be produced which may be more easily separated from solution, for example by cooling to precipitate microgels of good crystallinity. In fact, the crystal structure of microgels produced according to the present process appears to be improved over those produced by known processes. That good microgels may be produced employing a process which is, at least in its initial stage, solvent-free is surprising. It has hitherto been assumed that the nature and presence of the solvent from the beginning of the polymerisation is essential in order to favour intramolecular cross-linking and to prevent macrogelation occurring. Furthermore, since the microgels of the present invention may be separated from the reaction solution without the need to add any further organic liquid, the possibility exists for reusing the polymerisation solvent directly. Water-soluble or insoluble microgels may be produced.

Polymerisation may also proceed at a faster rate using the solvent-free first step of the present invention, compared to conventional processes without this step. Thus, the speed of production of the microgels may be enhanced.

The polymerisation reaction of the present invention may be an addition polymerisation, for example a cationic, anionic or free radical polymerisation, or a step-growth or condensation polymerisation. The polymerisable monomer may in particular be any of those monomers disclosed in U.S. Pat. No. 5,863,996 filed on Jun. 7, 1995.

However, the present invention is advantageously applied to the production of polyurethane microgels. In this case, the monomer is a dihydroxy or polyhydroxy compound, such as a polyalkylene oxide, particularly polyethylene oxide or polypropylene oxide. Generally, the ratio of number average molecular weight to functionality is greater than 1,000. Polyethylene glycols of number average molecular weight 3,000 to 10,000 are particularly preferred. Production of water-insoluble polyurethane microgels tends to be favoured by using relatively low amounts of polyethylene oxide and relatively high amounts of cross-linking agent. Water soluble microgels may be made in converse manner.

Cross-linking may be carried out using a suitable cross-linking agent known in the art, such as a diisocyanate or polyisocyanate, for example a (cyclo)aliphatic, araliphatic or aromatic diisocyanate. Specific examples include 2,4 and 2,6 toluene diisqcyanate; (cyclo)aliphatic diisocyanates such as 1, 6 hexamethylene diisocyanate, isophorone diisocyanate, 4, 4'-dicyclohexylmethane diisocyanate, and (cyclo)hexylene 1, 2- and 1,4-diisocyanate; and araliphatic diisocyanates such as 4,4'-diphenylmethane diisocyanate.

In order to provide a three-dimensional branched polyurethane structure, the polymerisation reaction preferably also includes a polyfunctional compound having active hydrogen atoms, such as an aromatic or aliphatic polyol, for example an aliphatic triol such as 1,2,6 hexantriol.

A particularly preferred polyurethane is formed by polymerising a mixture of a polyethylene glycol, an aliphatic triol, and a diisocyanate in a molar ratio 1:1–8:2–15.

The solvent for the second step may in principal be any suitable solvent, such as those disclosed in GB2090264. Preferably, the solvent will have a moderate solubility for the microgel at ambient temperature, such as to allow the microgel to be precipitated directly from solution without the addition of any other substance thereto which would affect the ability of the solvent to be directly reused in a further polymerisation reaction. Methyl ethyl ketone is a particularly preferred solvent for the production of polyurethane microgels. Acetone and diethyl ketone may also be employed. The solvent is employed in the second step of the polymerisation process, and is generally added such as to dilute the reaction mixture from the first step to a concentration in the range 2 to 30%, preferably 5 to 20% wt/volume.

The properties of the finished microgels are dependent upon the extent of polymerisation which occurs during the first step in the absence of solvent. Generally, the first step is carried out for a time which is insufficient for macrogelation to occur and this is usually in the range 1 to 60 minutes, preferably 5 to 30 minutes, and particularly 10 to 20 minutes. Generally, the reaction to completion in the second step as indicated by the disappearance of cross-linking agent takes less than 24 hours. Thus the first step may take from about 0.5 to 2.0% of the total polymerisation time. A polyurethane will generally be produced by polymerisation at a temperature in the range 50 to 100° C.

Microgels of the present invention generally have higher weight average molecular weights (e.g. above 40,000, typically in the range 100,000 to 200,000) than those prepared conventionally without the solvent-free first step.

The microgel particles of the present invention tend to flow well and be less sticky than conventional microgels, and be of good size uniformity. This may be due to differences in chemical structure arising from the solvent-free first step. Polyethylene oxide-based microgels are believed to comprise a hydrophobic core (composed for example in the case of a polyurethane primarily of aromatic moieties and polyol) and hydrophilic loops or side chains extending therefrom formed of polyethylene oxide. In the microgels of the present invention the loops or chains may be longer due to some linear polymer formation prior to cross-linking.

The microgel is preferably separated from solution by cooling the reaction mixture to a temperature below the temperature it which polymerisation is carried out, and below the melting temperature of the crystalline portion of the microgel. For an industrial process, deposition of the solid microgel is preferably brought about at a temperature of 10 to 25° C. i.e. substantially room temperature; although cooling below room temperature may be used if necessary.

The microgels of the present invention have a particularly high degree of crystallinity, which may be in the range 40 to 70% determined as described herein. Generally, the microgels crystallise in the form of granules comprising globular microgel particles whose size shows good consistency. Thus, the average granule size may be in the range 10 to 1,000 microns determined as described herein. Generally, the microgels are crystallised from solution in the form of granules having a sille greater than 0.1 mm, particularly 1 to 5 mm. Such microgel granules have beneficial compaction properties so as to be suitable for compression moulding. Generally speaking, the microgel granules produced by the production process may be used directly, without any need for further treatment such as grinding or sieving.

Thus, the microgel granules of the present invention are particularly suited to the production of solid sustained release devices produced by compression, optionally under the effect of heat. Generally, the sustained release device includes an active agent which is dispersed uniformly throughout the microgel compress. The sustained release device is intended to be placed in a liquid into which the active agent is to be released, such as water. The microgel itself may be either soluble or insoluble in the liquid in which the active agent is to be released. In the case of insoluble microgels, the liquid may gain access to the active agent through pores present in the microporous compress.

It is a surprising property of the microgels of the present invention that they are able to produce a compress which on swelling in water does not disintegrate but becomes microporous. Compression may be carried out at room temperature and heating is not generally required.

However, the microgels can generally be melted at temperatures of less than 100° C. without decomposition, and this allows moulded forms to be produced.

The active agent may be a pharmaceutical, bacteriostat, viricide, insecticide, herbicide, larvicide, fungicide, algicide, nematicide, anthelmintic, topical or dermatological agent, anti-foulant for marine growth prevention, enzyme, preservative, surfactant, pigment, disinfectant, sterilising agent or any other agent for which sustained release is desirable. It is a particular benefit that the microgel sustained release device of the present invention may be used to deliver high molecular weight active agents, such as biologically active molecules, particularly proteins. Since proteins and many peptides have high molecular weight and hydrophilicity, it has hitherto been difficult to find materials which can regulate the release of these substances. Although hydrogels have special potential for the release of proteins due to their relatively high permeability, hydrophilic nature and biocompatability, introducing a protein into a hydrogel matrix has hitherto proved to be difficult. Prior methods have included polymerisatiorn of the hydrogel in the presence of the protein or peptide, or loading the protein or peptide into the hydrogel by swelling the hydrogel in an aqueous solution thereof and subsequently drying again. However, both these methods have disadvantages and may lead to toxic reaction products or a denatured protein. The microgels of the present invention allow production of a hydrogel matrix by compaction of microgel granules admixed with the active agent at room temperature in the dry state. This minimises possible degradation or contamination of the protein or peptide. Previously compaction of microgels generally required heating.

In particular, the protein or peptide may be an antibody, an enzyme or a hormone. A microporous sustained release device may also deliver a living micro-organism, such as a bacterium (for example lactobacillus) or a parasitic organism, such as those used to kill fungi or mosquito larvae.

Water-soluble microgels may be used to deliver such biologically active materials. They may also be used to aid solubility of an insoluble or sparingly soluble active agent.

The compressed or moulded microgel may be in any suitable solid form, such as a tablet or ball, cylinder, disc or block. The microgel solid form may be coated with a coating which is soluble or insoluble in the liquid into which the active agent is to be released. In the case of an insoluble coating, a suitable aperture or apertures will be provided to allow ingress of liquid and release of active agent.

BRIEF DESCRIPTION OF DRAWINGS

FIG. 4 shows the release of caffeine from tablets made by melting and compressing microgel samples x4-5-3, x3-5-3 and x2.5-5-3.

DETAILED DESCRIPTION OF PREFERRED EMBODIMENTS

Figure 1:
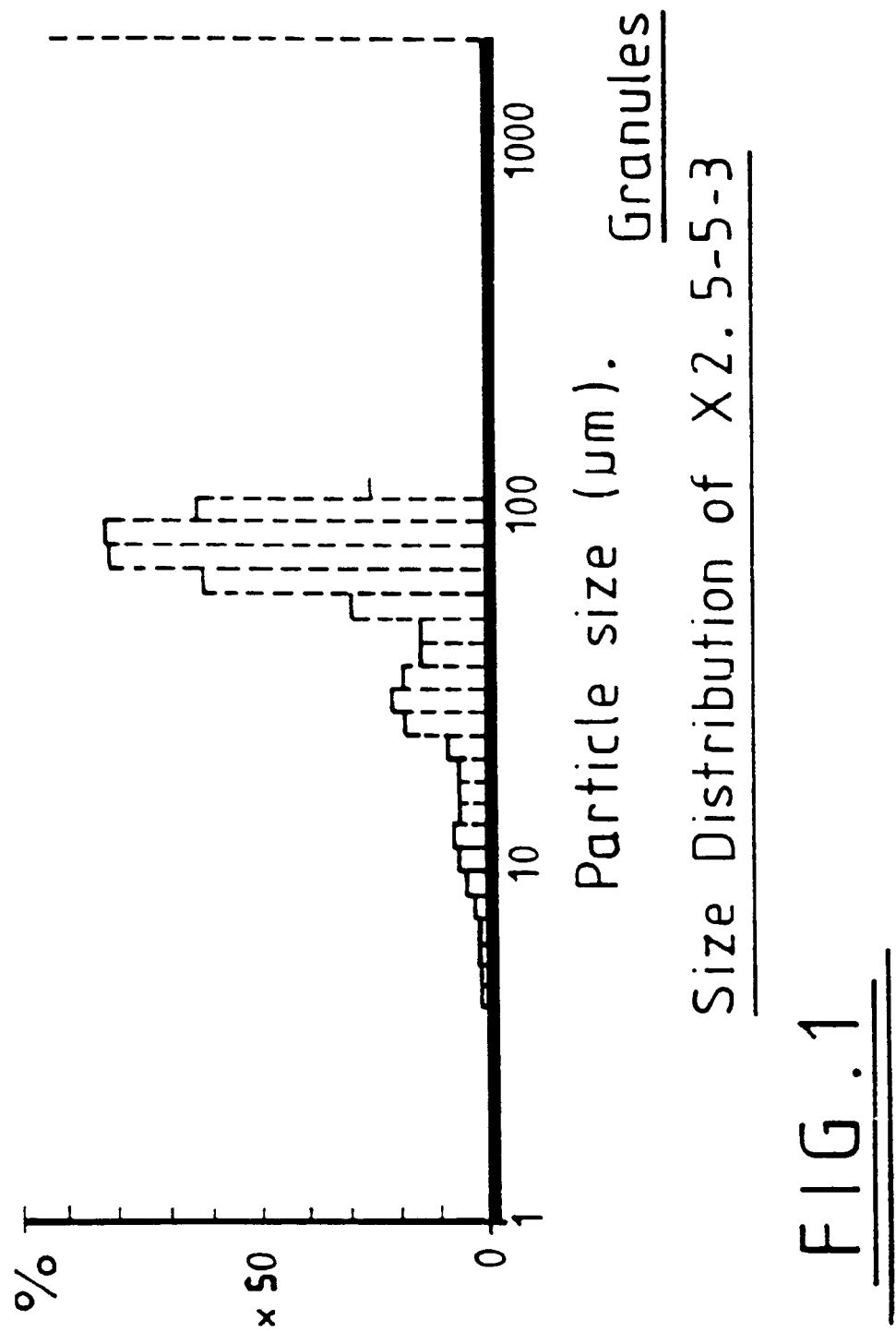
FIG. 1 shows the distribution of particle sizes of microgel granules for the sample x2.5-5-1.

Embodiments of the invention will now be described by way of example only

EXAMPLE 1 (Synthesis of microgels)

(i) The following materials were employed. PEG 6000 (Polyethylene glycol; the code 6000 represents the approximate molecular weight) was supplied by BP and was vacuum dried at 90–95° C. for at least 4 hours using a Rotavapor (trademark) drier and was stored molten in an oven at 80° C. until used. The hydroxyl numbers of the dried PEGs were determined by a standard method. The number average molecular weight value calculated from these hydroxyl numbers was 5830. Desmodur W (dicyclohexyl methane diisocyanate) was obtained from Bayer and was used without further purification. 1,2,6-hexantriol (HTP) was provided by Aldrich and used without further purification.

Caffeine (Aldrich, Mw: 235), bovine serum albumin (BSA) (obtained from Sigma, Mw:66,000) and polyvinyl pyrrolidone (Aldrich, Mw: 10,000) were used as model drugs for controlled drug delivery.

Methyl ethyl ketone (MEK) was supplied by Aldrich and was dried over anhydrous calcium sulphate (20–40 mesh) and molecular sieve (4A type, 20 mesh) for at least 24 hours and distilled fresh before use. The solubility parameter of MEK is 18.4 $J^{1/2}ml^{-1/2}$.

Chloroform and petroleum ether (60–80° C. b.p.) were used as supplied by Aldrich.

Anhydrous ferric chloride (FeCl$_3$) supplied by BDH was used as catalyst.

Wheaton glass serum bottles and their corresponding seals with teflon-faced septum were supplied by Aldrich and were used as the reaction container.

(ii) Microgel samples were prepared using the following route. The initial reactions were carried out in solvent-free bottles and then the reactants were diluted with solvent after various initial reaction times. Molten PEG6000 was weighed in a bottle and there was added thereto hexantriol in which anhydrous FeCl$_3$ was dissolved. The concentration was monitored so to give a concentration of FeCl$_3$ in the total reactants of 0.2 mg/g. These reactants were mixed together and then Desmodur W was added. The bottle was placed in an oven at 80° C. and samples were withdrawn at different times, e.g. 5 mins, 10 mins, 15 mins, 20 mins and 25 mins. In a second step the samples were diluted in methyl ethyl ketone to different concentrations, i.e. 5.8, 8.7 and 11.6% (wt./vol.). Additional catalyst was included in the solvent used for dilution, so the total concentration of the catalyst in the solution was 0.5 g/100 ml. The solutions sealed in the bottles were put back in the same oven for further reaction. (The samples withdrawn at 20 mins and marked with an asterisk were actually macrogeled before dilution, and fall outside the present invention.)

Results are shown in Table 1 where Ti represents the initially solvent-free reaction time. The molar ratio is PEG: hexantriol: Desmodur W.

TABLE 1

Samples of Solvent-Free Initial Reaction.

| SAMPLE | Ti(min) | Molar Ratio | Solvent | Concentration |
|---|---|---|---|---|
| X4-5-3 | 5 | 1:4:7 | MEK | 11.6 |
| X4-10-3 | 10 | 1:4:7 | MEK | 11.6 |
| X4-15-3 | 15 | 1:4:7 | MEK | 11.6 |
| X4-20-3 | 20* | 1:4:7 | MEK | 11.6 |
| X3-5-3 | 5 | 1:3:5.5 | MEK | 11.6 |
| X3-10-3 | 10 | 1:3:5.5 | MEK | 11.6 |
| X3-15-3 | 15 | 1:3:5.5 | MEK | 11.6 |
| X3-20-3 | 20* | 1:3:5.5 | MEK | 11.6 |
| X2.5-5-3 | 5 | 1:2.5:4.75 | MEK | 11.6 |
| X2.5-10-3 | 10 | 1:2.5:4.75 | MEK | 11.6 |
| X2.5-15-3 | 15 | 1:2.5:4.75 | MEK | 11.6 |
| X2.5-20-3 | 20* | 1:2.5:4.75 | MEK | 11.6 |
| X1.5-5-3 | 5 | 1:1.5:3.25 | MEK | 11.6 |
| X1.5-10-3 | 10 | 1:1.5:3.25 | MEK | 11.6 |
| X1.5-15-3 | 15 | 1:1.5:3.25 | MEK | 11.6 |
| X1.5-20-3 | 20 | 1:1.5:3.25 | MEK | 11.6 |

The completion of the reaction was indicated by the disappearance of the isocyanate IR peak at 2225 cm$^{-1}$. The reaction will normally take less than 24 hours. All the microgels were insoluble in water and soluble in chloroform.

Samples marked * are for comparison only.

EXAMPLE 2 (Crystallisation)

Microgel granules were prepared by direct filtration of a microgel solution after leaving the solution in a freezer at −15° C. for 20 minutes. The microgel and the solvent were easily separated. Because there was still some solvent left in the filtered samples a small amount of petroleum ether (60–80° C.) was used to wash the separated microgel samples. Washing prevented the flocculation of crystallised granules from sticking together. The samples were then dried in a vacuum oven overnight. The amount of microgel recovered from the crystallisation was well above 96% excluding the loss of materials during work-out.

The particle sizes of the microgel granules were measured using a Malvern 2600 model laser scattering particle sizer. Results are shown in Table 2.

FIG. 1 shows the distribution of particle sizes for sample X2.5-5-1. Comparing the results shown in Table 2, the higher the concentration of monomers, the bigger the average particle size of the crystallised granules. The change of the specific area as the monomer concentration changes also reflect the same trend. The particle sizes, on the other hand, were quite uniform for each sample.

TABLE 2

| SAMPLE | Conc. of Monomer (g/100 ml) | Specific Area (sq m/cc) | Average Size ($\mu$m) |
|---|---|---|---|
| X2.5-5-1 | 5.8 | 0.1422 | 66.51 |
| X2.5-5-2 | 8.7 | 0.0987 | 72.21 |
| X2.5-5-3 | 11.6 | 0.0946 | 73.52 |

EXAMPLE 3 (characterisation)

1) Molecular Weight and Molecular Structure

GPC (Gel Permeation Chromatography) was used to measure the molecular weight of the microgel samples. The experiments were carried out using following conditions:

a) Waters Model 510 pump, 1.0 ml/min, 600–800 psi b) Knaur Differential Refractometer c) Waters WISP 710B automatic sample injector, injection volume 100 $\mu$l.

d) Waters 745 data module e) Waters Ultrastyragel-linear and Ultrastyragel-500A columns.

Sample concentration was 0.1 g/100 ml. Sample solutions were filtered before injecting into the gel permeation chromatograph using a Waters disposable 0.54 $\mu$m filter. Chloroform was employed as the solvent.

The system was calibrated with polyethylene glycol standards which were supplied by Polymer Laboratory Ltd.

The molecular weight of the microgels prepared via the "solvent-free" route of the present invention was much higher than that of the microgels prepared by conventional solution polymerisation. All the samples had a single peak on a GPC curve which indicated that the composition of each microgel sample was uniform. Or in other words, they were all intramolecularly crosslinked but had different sizes. The total reaction could be divided into a) initial stage reaction in the absence of solvent, and b) further reaction in solution after solvent was added.

Both steps were essential to form such microgels as the first step reaction (because of the high reactant concentration) should be faster and effective, so long as the crosslinking was still microscopic, till solvent was added. Macrocelation is probably avoided by steric stabilization provided by PEG chains chemically anchored around the microgel cores.

TABLE 3

| | Molecular Weight | | |
|---|---|---|---|
| SAMPLE | Mw | Mn | Mw/Mn |
| X2.5-5-3 | 169516 | 92478 | 1.83 |
| X2.5-10-3 | 115411 | 42712 | 2.70 |
| X2.5-15-3 | 130466 | 43844 | 2.97 |

2) Glass Transition and Crystallinity

DSC (Differential Scanning calorimetry) experiments were carried on a DuPont Model 910 DSC instrument coupled with a DuPont Model 990 thermal analyser. Some 3–5 mg of sample was transferred to an aluminium pan. The pan was then sealed hermetically and heated from the starting temperature to a limit temperature at a rate of 5° C./min as stated later. The DSC cell was constantly purged with dry nitrogen gas to avoid moisture contamination during the operation.

The DSC characterisation results are losted in Table 4. The experiments were carried out at a heating rate of 5° C./min. Data for PEG6000 polyethylene oxide is included for comparison.

TABLE 4

| | DSC Results. | | | | |
|---|---|---|---|---|---|
| SAMPLE | Tg (° C.) | Tm (° C.) | $\Delta H_f$ J·g-1 | PEG w/w % | Crystallinity |
| X3-5-3 | −120.34 | 51.18 | 110.7 | 76.0 | 66.2 |
| X3-10-3 | −115.42 | 46.37 | 68.22 | 76.0 | 40.8 |
| X2.5-5-3 | −114.53 | 50.25 | 99.61 | 78.7 | 57.5 |
| X1.5-5-3 | −106.21 | 51.48 | 120.5 | 84.7 | 64.6 |
| X1.5-5-3 | −113.9 | 48.52 | 88.70 | 84.7 | 47.6 |
| X1.5-10-3 | −108.93 | 52.99 | 105.8 | 84.7 | 56.7 |
| PEG6000 | −94.37 | 65.68 | 219.0 | 100 | 99.5 |

The glass transition of the microgel should be determined mainly by the soft segment of each microgel molecule which was composed of PEG chains; since the quantity of the hard core, i.e. urethane bonds and crosslinkers, was quite low (the weight percentage of these components was normally less than 15%). The structure of each microgel molecule is assumed to comprise a central core having anchored thereto PEG chains or loops.

The degree of the crystallinity of the microgels and the PEG can be measured by measuring the heat of fusion which is related to the melting of crystalline PEG in microgel samples.

$$\Delta H_f = \frac{A}{m} BO$$

m: sample mass in mg

A: area of the curve in cm$^2$

Bo: instrumental constant $\Delta H_f$: heat of fusion in J.g$^{-1}$

The heat of fusion of 100% crystalline PEO (polyethyleneoxide) was taken as 220.12J.g$^{-1}$. By dividing the heat of fusion of each microgel by the heat of fusion of the 100% PEO, the degree of the crystallinity in the total polymer was obtained. The degree of crystallinity in the PEO fraction of the microgel was further calculated, taking account of the proportion of PEG in each microgel.

EXAMPLE 4 (Controlled Drug Delivery)

1) Tablets made by Direct Compression

Figure 2:
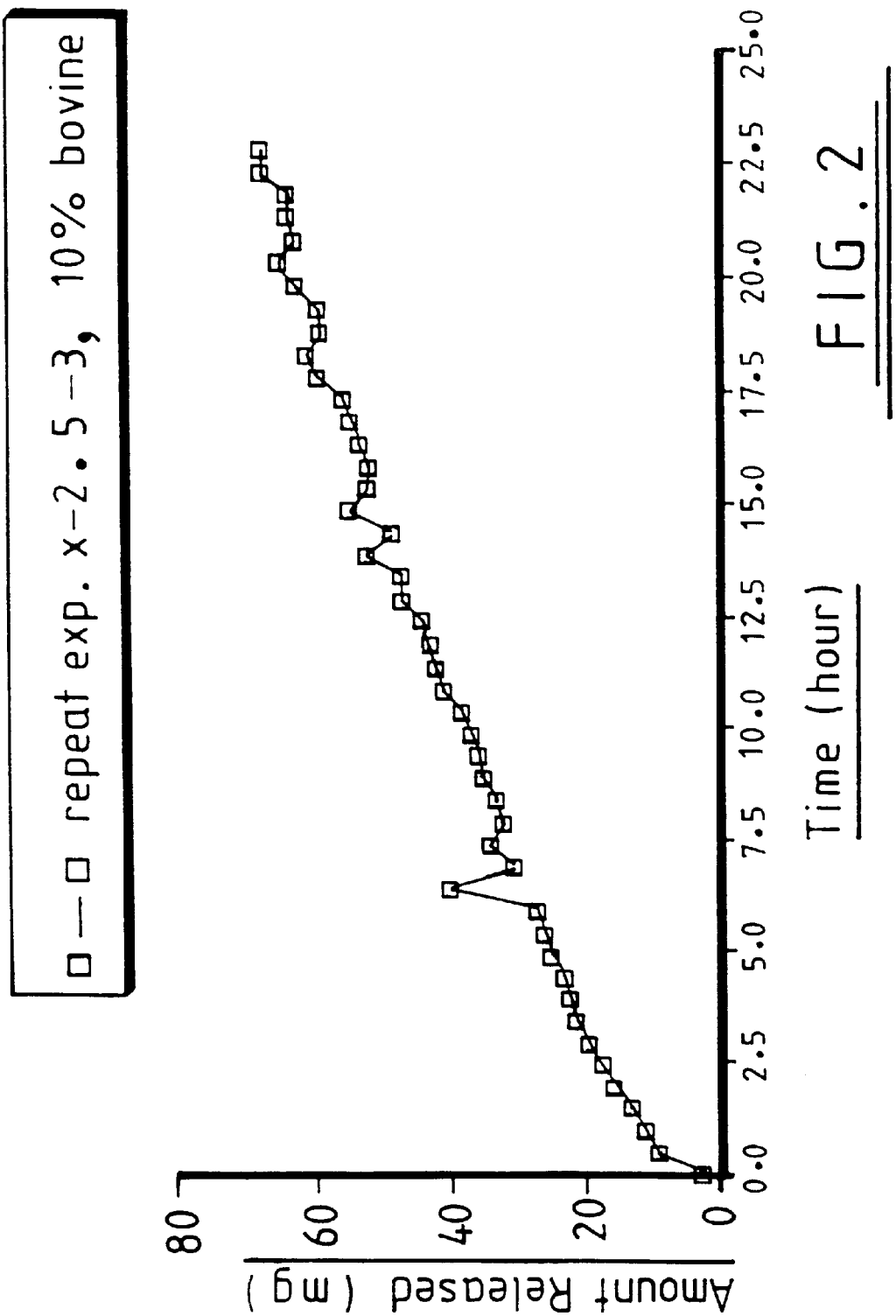
FIG. 2 shows the release of bovine serum albumin (BSA) from a tablet of microgel made by direct compression.
Figure 3:
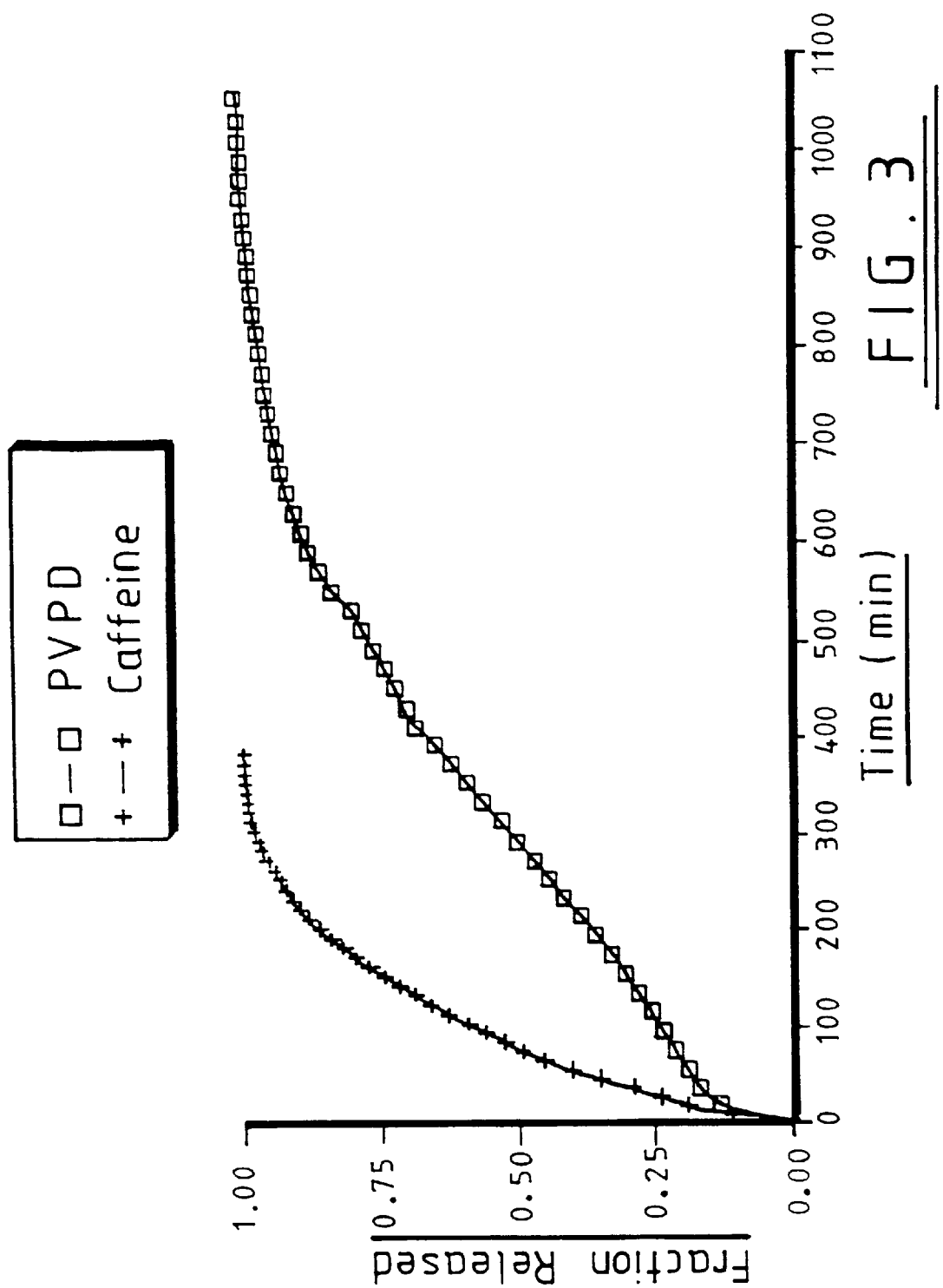
FIG. 3 shows the release of polyvinyl pyrrolidine (PVDP) and caffeine from a tablet of microgel made by direct compression.

FIGS. 2 and 3 show the release of bovine serum albumin (BSA), polyvinyl pyrrolidone (PVDP) and caffeine from a tablet. The tablets were made by direct compression of a mixture of microgel X2.5-3 and each model drug. The loading was 10% (w/w) and the pressure applied was 5 tons. The size and the weight of the tablets were: diameter 13 mm and thickness 3 mm, and 0.5 grams respectively. Release experiments were carried out in a standard dissolution apparatus at 37° C. in water. Paddle speed was 60 rpm. The release of bovine serum albumin, PVDP and caffeine were monitored by UV absorption at 280 nm, 215 nm and 274 nm respectively.

The tablets were insoluble in water, and did not disintegrate even at the end of the release experiment but did swell. A typical swollen tablet measured 20 mm diameter×60 mm thickness.

2) Tablets Made by Melting and Compressing

Tablets could also be made by a melting and compressing process. Thus, a mixture of the microgel and a drug such as caffeine which is stable at elevated temperature was heated to 80° C. for 20 minutes. The molten mixture was then compressed to form tablets or balls using a special mould. The so-prepared tablets swell in water and will normally provide a more prolonged release than those prepared by direct compression. Release profiles are shown in FIG. 4.

This method of preparing tablets may form the basis of an economical high-speed production of constant-release swelling devices using conventional tabletting equipment. This kind of tablet could also be injection moulded.

It is surprising that the microgel tablets made by either direct compressing or by melting and compressing do not disintegrate when immersed in water for a long time. The crystallinity and the intermolecular entanglement of the microgel may play an important role in this.

Another feature for these tablets is that the rate of release of high molecular weight substances, i.e. PVDP and BSA, from the microgel tablets is relatively high. Without wishing to be restricted to any particular scientific theory, this could be attributed to a different release mechanism. For conventional non-porous hydrogels, diffusion via free volume governs the rate of the release. Hence substances of different molecular weights have quite different release rates. The higher the molecular weight the slower the release. For microgel tablets, small channels ranging from 1 μm within the tablets have been seen in electromicrographs. These channels can then provide faster release for the high molecular weight agents than would be obtained using non-porous hydrogels.

We claim:

1. A process for producing a microgel comprising:
   subjecting, in a first step substantially free of solvent for the essential reactants required for the formation of the microgel in a cross-linking polymerization reaction, at least one monomer to a polymerization reaction consisting essentially of a cross-linking polymerization reaction, said at least one monomer being present in a reaction mixture at a concentration favoring intermolecular cross-linking; and thereafter,
   dissolving, in a second step initiated before macrogelation can occur, the reaction mixture with a solvent to a reduced concentration favoring intramolecular cross-linking, said solvent being substantially non-reactive in said cross-linking polymerization reaction, and said cross-linking polymerization allowed to proceed further, so as to produce a microgel.

2. A process according to claim 1 wherein said microgel is a polyurethane microgel.

3. A process according to claim 1 wherein said at least one monomer is a polyalkylene oxide.

4. A process according to claim 3 wherein said polyalkylene oxide is a polyethylene glycol of number average molecular weight in the range from about 3000 to about 10,000.

5. A process according to claim 3 wherein the polyalkylene oxide is cross-linked by means of a diisocynate.

6. A process according to claim 1 wherein there is provided at least one polyfunctional compound selected from the group consisting of aromatic and aliphatic polyols, for promoting branching to form a branched polyurethane.

7. A process according to claim 6 wherein the polyfunctional compound is an aliphatic triol.

8. A process according to claim 7 wherein there are provided a polyethylene glycol, an aliphatic triol and a diisocynate for reaction in the cross-linking polymerisation reaction.

9. A process according to claim 8 wherein the molar ratio of polyethylene glycol to triol to diisocyanate is 1:1 to 8:2 to 15.

10. A process according to claim 1 wherein the solvent for said second step has a solubility for the microgel at ambient temperature, such as to allow the microgel to be precipitated directly from solution without the addition of any other substance to effect precipitation.

11. A process according to claim 1 wherein there is added an amount of said solvent such as to dilute said reaction mixture to a reduced concentration of from 2 to 30% wt/volume.

12. A process according to claim 1 wherein said first step is carried out for a time period of 1 to 60 minutes.

13. A process according to claim 12 wherein said time period is from 5 to 30 minutes.

14. A process according to claim 1 wherein said cross-linking polymerisation is carried out at a temperature of 50 to 100° C.

15. A process according to claim 10 wherein precipitation of the microgel is achieved by cooling the reaction mixture to a temperature in the range of from 10 to 25° C.

16. A process according to claim 1 wherein said cross-linking polymerization is carried out so as to produce a microgel having a weight average molecular weight above 40,000.

17. A process according to claim 16 wherein said weight average molecular weight is in the range from 100,000 to 200,000.

18. A sustained release device comprising a microgel produced by a process according to claim 1 and an active agent capable of being released from said microgel.

19. A device according to claim 18 which device is in the form of a solid body formed of a compress of microgel granules.

20. A device according to claim 18 wherein the active agent is a protein or peptide.

21. A process according to claim 1 further characterised in that no cross-linking polymerization reactant is added in said second step.

22. A process according to claim 1 which process is substantially anhydrous.

23. A process according to claim 11 wherein said reaction mixture is diluted to a reduced concentration of from 5 to 20% w/v.

24. A process according to claim 10 which includes the further step of precipitating the microgel out of solution by cooling thereof.

25. A process according to claim 24 in which is produced a microgel having a crystalline portion, wherein the reaction mixture is cooled to a temperature below the temperature at which said cross-linking polymerization reaction is carried out and below the melting temperature of the crystalline portion of the microgel.

26. A process according to claim 24 wherein the solvent is recovered after precipitation for reuse without further processing.

27. A process according to claim 24 which is carried out so as to produce microgel granules having a granule size of from 0.01 to 5 mm.

28. A process according to claim 27 wherein said granule size is from 1 to 5 mm.

29. A device according to claim 18 wherein said active agent is a living microorganism.

30. A device according to claim 18 wherein said active agent is selected from the group consisting of pharmaceuticals, bacteriostats, viricides, insecticides, herbicides, larvicides, fungicides, algicides, nematicides, anthelmintics, topical or dermatological agents, anti- -foulants for marine growth prevention, enzymes, preservatives, surfactants, pigments, disinfectants, and sterilizing agents.

31. A device according to claim 18, wherein said device is in the form of a solid body formed by melting and compressing the microgel.

32. A device according to claim 31 wherein the solid body is formed by heating the microgel to 80° C. for 20 minutes.

33. A device according to claim 31 wherein said solid body is formed by injection moulding.

* * * * *

UNITED STATES PATENT AND TRADEMARK OFFICE
CERTIFICATE OF CORRECTION

PATENT NO. : 5,994,492

DATED : November 30, 1999

INVENTOR(S) : Graham et al.

It is certified that error appears in the above-identified patent and that said Letters Patent is hereby corrected as shown below:

Column 9, line 53, "claim 1" should read --claim 2--.

Signed and Sealed this

Eighth Day of August, 2000

*Attest:*

Q. TODD DICKINSON

*Attesting Officer*  *Director of Patents and Trademarks*